United States Patent
Horvath

(10) Patent No.: US 8,459,993 B2
(45) Date of Patent: Jun. 11, 2013

(54) COVER AND HOLDBACK ELEMENT FOR PERMITTING DISTURBANCE-FREE DENTAL OPERATIONS TO BE PERFORMED ON TEETH

(75) Inventor: Domonkos Horvath, Jestetten (DE)

(73) Assignee: Ivoclar Vivadent AG, Schaan (LI)

( * ) Notice: Subject to any disclaimer, the term of this patent is extended or adjusted under 35 U.S.C. 154(b) by 487 days.

(21) Appl. No.: 11/186,528

(22) Filed: Jul. 21, 2005

(65) Prior Publication Data

US 2006/0223028 A1 Oct. 5, 2006

(30) Foreign Application Priority Data

Apr. 4, 2005 (DE) .......................... 10 2005 015 406

(51) Int. Cl.
*A61C 5/14* (2006.01)
(52) U.S. Cl.
USPC .......................................................... 433/136
(58) Field of Classification Search
USPC ..... 433/29, 136–140; 600/236–238; 128/849, 128/850, 859, 861
See application file for complete search history.

(56) References Cited

U.S. PATENT DOCUMENTS

| | | | |
|---|---|---|---|
| 4,828,491 A | 5/1989 | Gray | |
| 5,524,644 A * | 6/1996 | Crook | 128/888 |
| 6,450,983 B1 * | 9/2002 | Rambo | 602/60 |
| 6,648,642 B1 | 11/2003 | Horvath | |
| 7,040,894 B2 | 5/2006 | Horvath | |
| 2004/0072126 A1 * | 4/2004 | Horvath | 433/138 |
| 2004/0097795 A1 * | 5/2004 | Horvath | 600/237 |
| 2005/0241647 A1 * | 11/2005 | Nguyen et al. | 128/856 |

FOREIGN PATENT DOCUMENTS

| | | |
|---|---|---|
| DE | 33 29 919 A1 | 4/1985 |
| DE | 299 06 369 U1 | 9/2000 |
| EP | 1 042 992 A2 | 10/2000 |
| WO | WO 89/09032 A1 | 10/1989 |
| WO | WO 02/096313 A1 | 12/2002 |

* cited by examiner

*Primary Examiner* — Sunil K Singh
(74) *Attorney, Agent, or Firm* — Woods Oviatt Gilman LLP

(57) ABSTRACT

A cover and holdback element for permitting disturbance-free dental operations to be performed on a patient's teeth includes an expandable sheet operable to cover at least a portion of the mouth volume of a patient and an intra-oral spanner and an extra-oral spanner. The sheet is turned around the at least one of the spanners and is displaceable relative thereto.

12 Claims, 7 Drawing Sheets

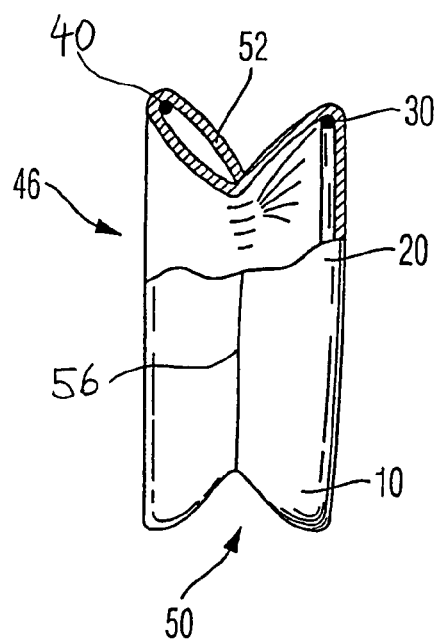
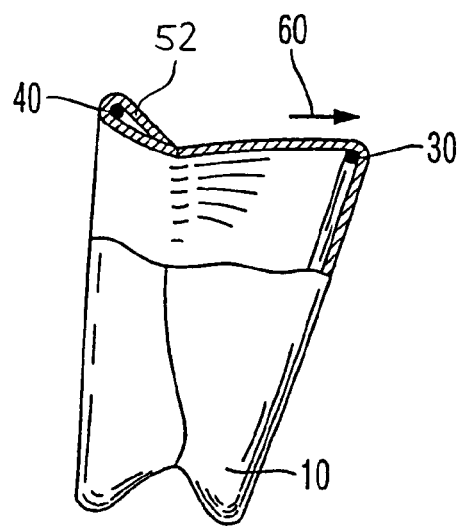
Fig. 4              Fig. 5
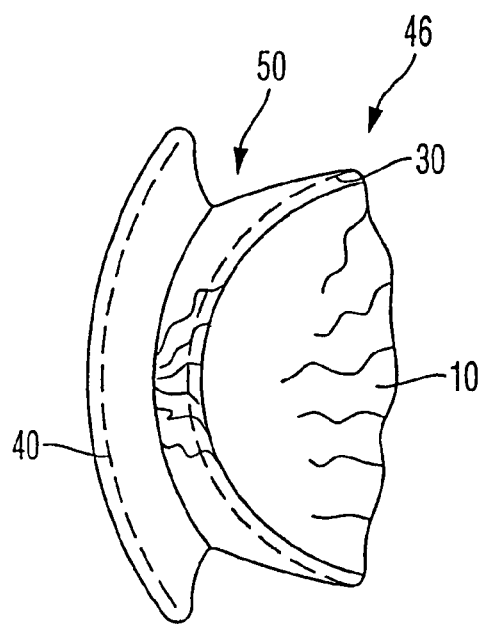
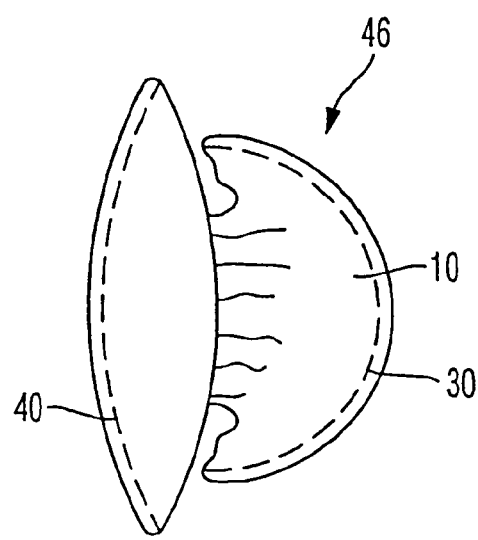
Fig. 6              Fig. 7

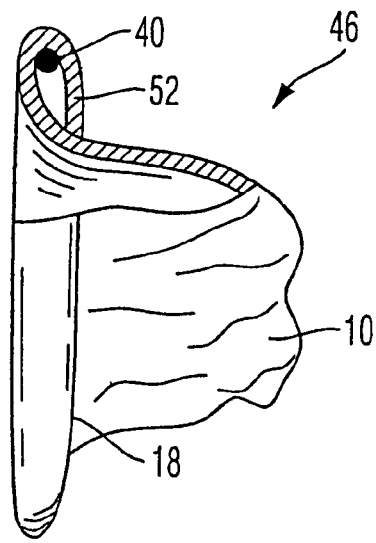
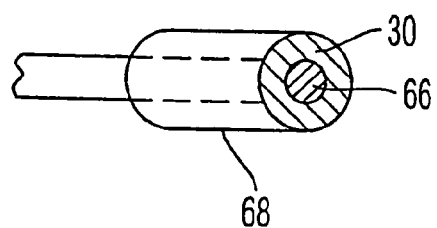
Fig. 9          Fig. 10
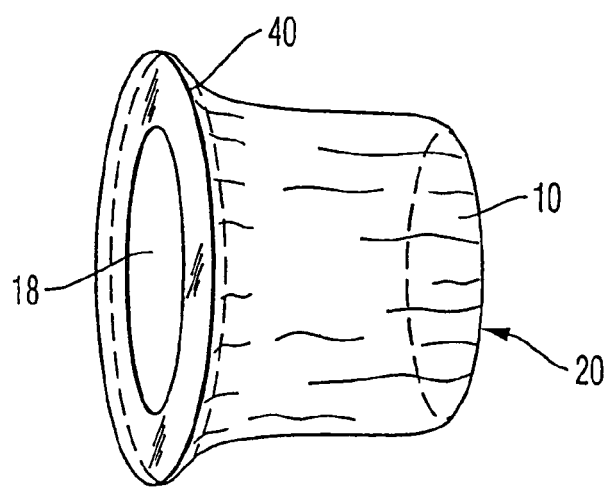
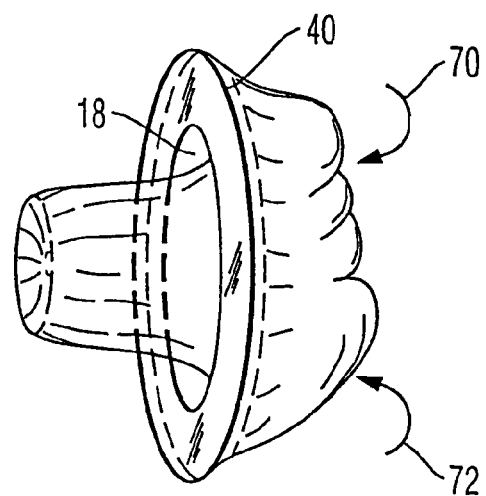
Fig. 11          Fig. 12

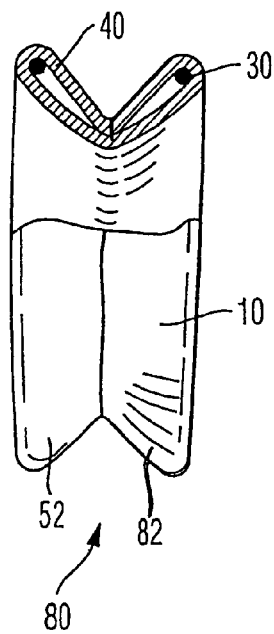
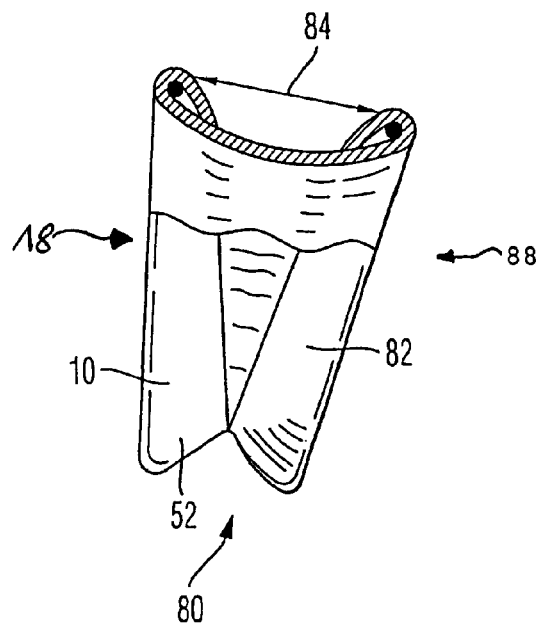
Fig. 17    Fig. 18
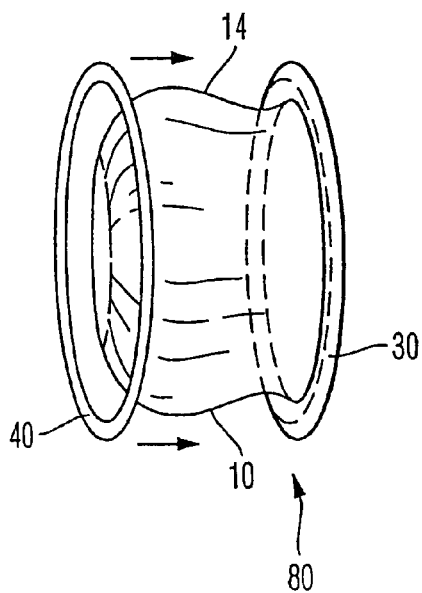
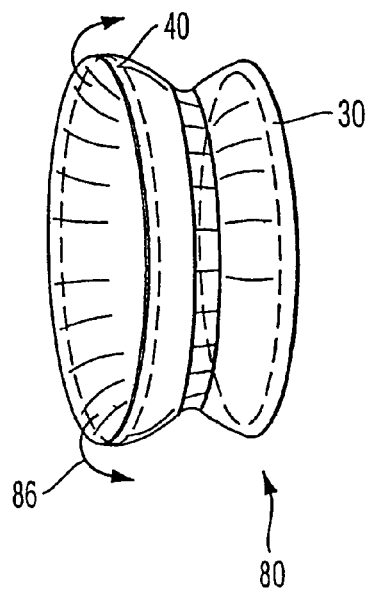
Fig. 19    Fig. 20

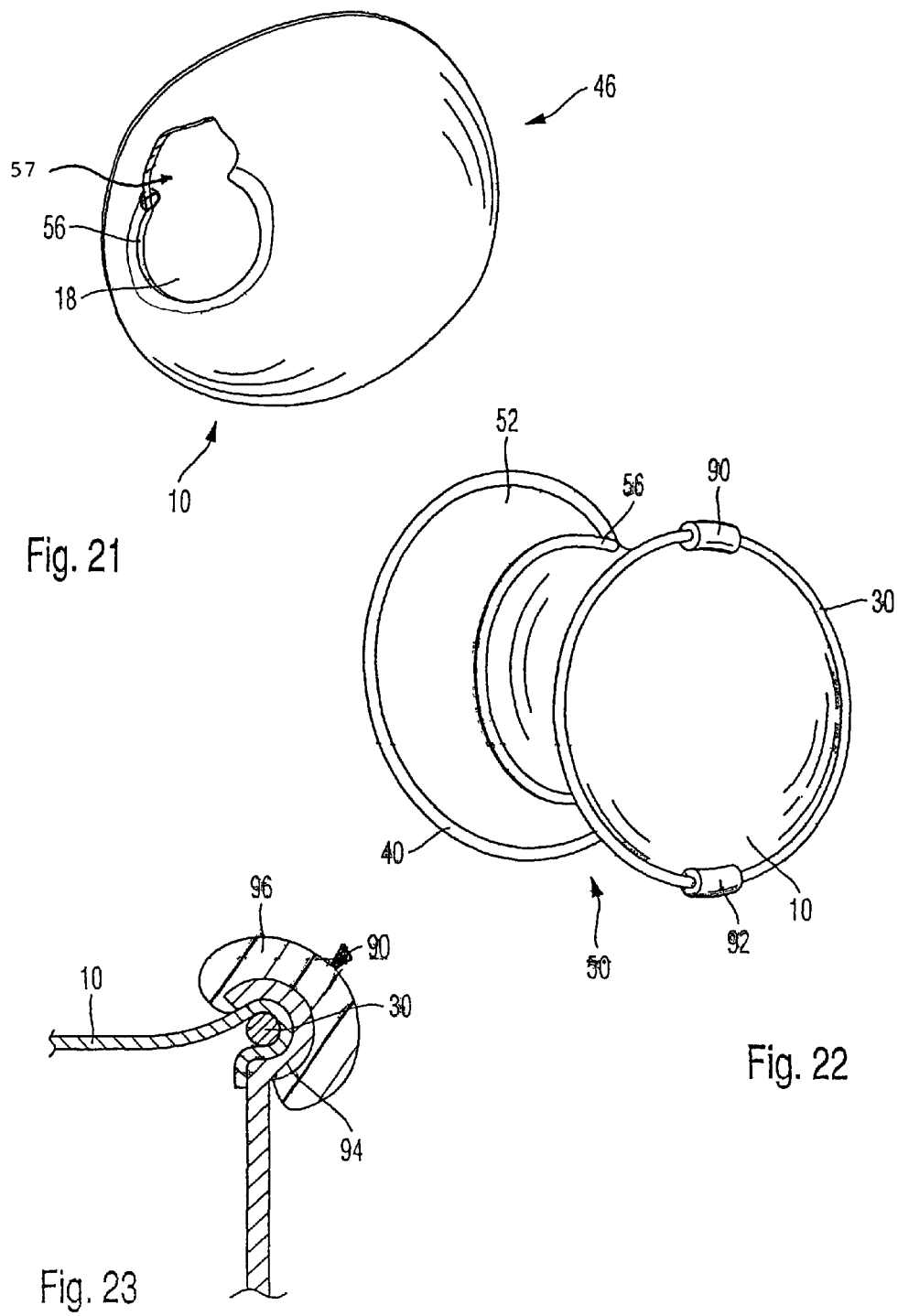

COVER AND HOLDBACK ELEMENT FOR PERMITTING DISTURBANCE-FREE DENTAL OPERATIONS TO BE PERFORMED ON TEETH

CROSS REFERENCE TO RELATED APPLICATIONS

This application claims foreign priority benefits under 35 U.S.C. §119 (a)-(d) from German patent application ser. no. 10 2005 015 406.9 filed on Apr. 4, 2005.

BACKGROUND OF THE INVENTION

The present invention relates to a cover and holdback element for permitting disturbance-free dental operations to be performed on teeth as well as a process for the production of such a cover and holdback element and, additionally, a method for using such a cover and holdback element.

Cover and holdback elements have been known for a considerable time. The cover and holdback elements serve to provide a dentist with an adequate ergonomic access to the teeth to be treated but, as well, protect the teeth against debris generated during dental operations including, as the occasion arises, detritus of the patients themselves generated during such dental operations.

Different elements have long been in use for holding back and covering such dental work regions. Thus, the lips and cheeks of the patients can be held back from the teeth to be treated via clamps or metallic instruments, for example. A more favorable approach, in contrast, involves a holder comprising an elastic sheet, such as is disclosed, for example, in WO 03/051185 A1. In connection with this approach, two tensioning elements in the form of rings are provided between which extend a sheet. The lips of the patient are held in tension via this sheet so that the mouth opening offers sufficient access for undertaking the dental work. A similar holder is known, as well, from DE 33 29 919 A1. In connection with this holder, protection of the lips of the patient is ensured, especially for sensitive patients. Also, in connection with this lip protection, an additional unit comprised of an elastic material can be provided on the lip ridges that additionally prevents a point- or narrow area-loading of the lips. A disadvantage in this connection is, however, that the teeth themselves are unprotected so that, in particular, debris may come into contact with the teeth.

In order to offer an improved covering, it is known to deploy a so-called coffer or rubber dam that, in contrast to a lip and cheek expander, is closed off on its back side via an elastic sheet. Solely the teeth or tooth to be handled is exposed via such a rubber dam so that the remainder of the mouth volume of the patient is protected.

An example of such an approach is shown in WO 98/034 559. In an approach of this type, a sheet is provided for configuring the rubber dam, the sheet being rolled extra-orally over a frame of known construction to form the rubber dam. Additionally, a further tensioning element is provided that also holds the sheet in a tensioned condition. In accordance with the respective requirements, the dentist can also cut the sheet to conform to a particular desired location and the desired handling on the exposed tooth or the respective tooth group can then be undertaken.

It is to be understood that the deployed sheet is subjected to considerable tension due to its particular configuration. In fact, a highly elastic material such as, for example, latex, can be used for the sheet so that, in principle, it need not be feared that the sheet will rip. Such sheets can be elastically expanded, for example by a factor of 7.

Due to the expansion of the sheet, however, there occurs, on the one hand, an increase in the force that is introduced and the tensioning elements for placing the rubber dam in tension must be configured in correspondingly form stable configurations.

On the other hand, a comparatively hard configuration of these elements is frequently perceived by patients as being unpleasant, in particular if the intra-oral spanner is hard.

A certain rough accommodation of the device to the mouth of the patient can be undertaken via the use of a material reserve, as is known from the above-noted publications. In this connection, the sheet material is rolled out from the frame of the rubber dam. The dentist can then estimate the required size and correspondingly unroll the sheet material and then begin the desired treatment. The disadvantage in this connection is that a certain amount of experience is required in order to gauge the appropriate disposition of the sheet.

This problem has been known for a while whereby, for example, U.S. Pat. No. 3,406,452 discloses a rubber dam frame, whereby a band that can be adjusted via a fastening means makes possible an appropriate sizing out of the sheet, at least along general lines.

As disclosed in U.S. Pat. No. 4,215,477, a rubber dam frame having pointed projections maintains the rubber dam sheet in a suitable manner under a pre-tension. On the other hand, the known solutions are not satisfactory; either the sheet is held in too strong a tensioned condition, which is disadvantageous from several points of view, or there occur folds in the sheet, or other disadvantageous events.

SUMMARY OF THE INVENTION

The present invention offers a solution to the challenge of providing a cover and holdback element for permitting disturbance-free dental operations to be performed on teeth, a production process for producing the cover and holdback element, and a method for using the cover and holdback element, wherein these cover and holdback element solutions make possible an improved ergonomic approach for the dentist and are cost favorable, yet ease the discomfort to patients during the handling or treatment of the teeth.

In accordance with the present invention, it is particularly advantageous that the inventive cover and holdback element is at the same time automatically and, in a three-dimensional sense, deformed, and accommodates itself to the shape of the mouth of the patient. This can be attributed to the particular special combination, in accordance with the invention, of the turning of the sheet, especially the turning of the sheet from the interior to the exterior, around the tensioning element and the displaceable disposition of the sheet relative to the tensioning element which is, preferably, an extra-oral spanner. The elastic sheet cinches radially inwardly with a certain pre-tension, is displaced via the shape of the mouth of the patient and, in fact, displaces to different extents around the circumference of the tensioning element.

Typically, the open mouth of the patient forms a symmetrically bent oval so that the sheet can displace without further intervention to the greatest extent possible on those positions having the greatest deviation from an annular shape. In accordance with the present invention, the sheet extends on both sides of the affected tensioning element, such as, for example, the affected extra-oral spanner and thereafter extends in a double walled manner inwardly to the lips of the patient, which, in addition to the urging provided by the sheet's own inherent tension, causes the sheet to arch radially inwardly. To this extent, the region of the cover and holdback element lying on the lips of the patient forms a cinched-in region that is annularly shaped or, as the case may be, is non-annularly shaped as well.

In accordance with the configuration of the inventive elements as a rubber dam, the sheet is closed off on its backside, while the sheet is, in a configuration thereof as a lip and cheek expander, again turned around the intra-oral spanner from the interior toward the exterior.

In accordance with the present invention, the cover and holdback element offers in each configuration, surprisingly, a sufficient wall tension as well to resist the suction of a suction element that is deployed during dental work. Due to the individual automatic accommodation of the cover and holdback element to the shape of the mouth of the patient, the possibility is provided to use a relatively firm and, thus, stable, sheet that is not sensitive to the suction effect of the suction element.

In accordance with the present invention, a sheet reserve is automatically provided at the turned around edge of the sheet. The sheet body can flow from this sheet reserve in a so-called after flow action, if a corresponding tension is exerted upon the sheet, whereby the sheet reserve can, as well, also automatically be drawn back in, if there exists an overflow of the sheet. This is attributable to the tendency of the sheet body to radially pull towards itself, as well, in those portions around which it is turned.

In accordance with the present invention, it is surprising that, even upon opening and closing of the mouth of the patient, an after flow of the sheet automatically occurs, whereby it is to be understood that preferably a sheet having a decidedly good sliding capability is chosen.

Talcum powder or talcum powder-free latex can be used as material for the sheet, or a suitable desired other material can be used such as, for example, polyurethane, polyethylene, nitrile, an elastomer, or another synthetic material. The sheet can also be configured of several layers, whereby it preferably has on its outwardly turned side a relatively low friction coefficient while the radially inward side is particularly clean.

While the disclosure herein is focused on a sheet, it is to be understood that another desired suitable planar cover medium can be used in lieu of a sheet such as, for example, a fabric, a coated fabric, a non-woven material, a coated non-woven material, or other suitable desired materials, whereby it is to be understood that, via the inventive measures, the material elasticity no longer plays so critical a role as has been the case with respect to the prior art, as the automatic accommodation of the material flow brings with it significant advantages.

In accordance with the present invention, it is particularly advantageous, as well, that the inventive fold edge practically stabilizes both tensioning elements and, in spite of the in-total three-piece construction, lends the inventive cover a unitary character.

In a further advantageous embodiment, it is provided that another form of the sheet body can be used. In this embodiment, the sheet body is substantially in the form of a ball. This form has the advantage that the formation of bubbles, as such can occur in a disposition of the sheet between planer surfaces, is reliablyly avoided. Due to the considerable elasticity of the deployed materials, no problem exists if, in lieu of a tube-shaped portion, a ball shape is used.

In another embodiment, solely the backside of the sheet body is spherically-shaped, while the tube-shaped portion is substantially cylindrical. Also, the occurrence of backside trapped air formation of bubbles is reliably foreclosed.

In a favorable embodiment, the tensioning elements are configured as rings. It is to be understood, however, that in lieu of such, clamps or wire can be used to assure the tension function, it being a precondition of such that suitable measures are taken to preclude damage to the material that may occur due to the open ends of such clamps or wires.

It is to be understood that annularly shaped rings formed of plastic or metal can be used for the tensioning element rings. The rings can also have an annular cross section or a suitable other desired cross section such as, for example, a diameter of, preferably, approximately 2 mm. Also, the tensioning element rings can be comprised of plastic-coated metal wires or spring steel wires and it is also possible to provide an at least partially coarse surface via a corresponding coating or other measures that increases the friction between the tensioning element rings and the sheet.

In another advantageous embodiment, it is provided that the largest open space of an opening that exists in the sheet body is greater than the smallest open space of the sheet body.

In another advantageous embodiment, it is provided that the edge of the sheet body that encircles the opening has the same wall thickness as the sheet, the edge being turned around outwardly, rolled up, thickened, or configured in the form of a collar, and the sheet body is closed off on the backside in a configuration thereof as a rubber dam, and the intra-oral spanner encircles the sheet radially from the outside.

In an additional embodiment, it is provided that the sheet body is held in an annular shape under tension via the tensioning elements and the free edge of the end of the sheet body that is turned around between the tensioning elements is disposed in tension and the free edge that encircles the opening of the turned around end of the sheet body radially cinches in the sheet between the tensioning elements.

In yet another advantageous embodiment, it is provided that the length of the cinched-in region relative to a tensioning element is variable and that the sheet body comprises a second opening in opposition to the first opening, and the sheet body passes partially through the intra-oral spanner and is turned around the intra-oral spanner due to an elastic expansion of the second opening toward the outside.

In an additional advantageous embodiment, it is provided that the tensioning elements are configured in an annular shape and, in particular, the intra-oral spanner comprises a diameter that is 2 to 20% and, especially, approximately 5 to 10%, smaller than that of the extra-oral spanner, and the sheet body has a wall thickness of 10 mm to 2 mm and/or the sheet body has an expansion capability to expand to 1.5 to 7 times its original size.

In an additional advantageous embodiment, it is provided that the tensioning elements are comprised of spring steel, plastic, and/or glass fibers, and especially, the tensioning elements have a cross section diameter of 0.5 to 5 mm, at least one tensioning element is at least partially encircled by an elastic material, and the sheet body comprises pre-stamped and/or pre-marked and/or perforated regions.

In a further advantageous embodiment, it is provided that the sheet body comprises at least one opening through which at least the extra-oral spanner is inserted into the sheet body and on which, adjacent the opening, the sheet body is positioned, and that subsequently a portion of the sheet body that is spaced from the opening is inserted through the first tensioning element and the opening, so that a bag-shaped portion results.

In an additional advantageous embodiment, it is provided that, especially in a further method step, an intra-oral spanner is passed through the extra-oral spanner and the opening of the sheet and ultimately disposed into the bag-shaped portion and the sheet is disposed in tension thereat, and the intra-oral spanner has a smaller diameter than that of the extra-oral spanner.

In a further advantageous embodiment of the present invention, it is provided that the sheet body is turned around the extra-oral spanner from the interior to the exterior and the turned around portion of the sheet body prestresses the sheet body in a cinched-in region, especially between the tensioning elements is a radially inwardly elastic manner.

In an additional embodiment of the present invention, it is provided that a substantially ball-or tube-shaped sheet body is prepared with two opposed openings and extends from the interior toward the exterior over rings including, especially, over an intra-oral spanner and an extra-oral spanner, so that the turned around portions radially cinch the sheet between the tensioning elements.

The edges come thereby into an outward disposition and, in fact, into an outward disposition in the cinched-in region. Also, in this connection, the play out of the sheet body regulates itself in correspondence with the anatomy of the patient, whereby, typically, in the lower lip region of the patient, a larger need for play out of the sheet is required than in an upper region of the patient and the mouth angle requires considerably more play out of the sheet than the upper lip region of the patient.

In an additional advantageous embodiment, it is provided that the sheet body is displaceable relative to at least the extra-oral spanner around which it is turned and the sheet, upon the application thereto of a pull force such as occurs upon the deployment of the sheet in the mouth of a patient, being, at the least, displaced toward one side of the extra-oral spanner, and especially being deformed.

In a further advantageous embodiment, it is provided that the length of the cinched-in region can also be varied on one side and that the sheet body, relative to the extra-oral spanner which is, especially, configured in an annular shape, can be displaced and is turned around the extra-oral spanner, and that the sheet body is turned outwardly around the extra-oral spanner and, especially, terminates in a rolled or thickened edge.

In a further advantageous embodiment of the present invention, it is provided that the sheet is turned around the intra-oral spanner from the interior toward the exterior and thus forms a lip and cheek expander.

In an additional advantageous embodiment of the invention, it is provided that a second tensioning element, in particular a tensioning element with a diameter less than that of the first tensioning element, is provided and is inserted through the opening in the first tensioning element, together with the pertaining portion of the sheet body, and that prior to the insertion of the sheet through the opening, the second element is placed on the sheet.

In an additional advantageous embodiment of the present invention, it is provided that the first tensioning element is the extra-oral spanner and the second tensioning element is the intra-oral spanner and that, in particular, the diameter of the extra-oral spanner is greater than that of the intra-oral spanner. In a further advantageous embodiment of the present invention, it is provided that the sheet body is prepared in an annular shape, especially, in a bulging or tubular shape, the sheet body extending between a first and second opening, and portions of the sheet body being turned one after the other around the tensioning elements from the interior toward the exterior and, especially, being turned around an intra-oral spanner and an extra-oral spanner, so that the turned around portions radially inwardly prestress the sheet body between the tensioning elements.

In a further advantageous embodiment of the present invention, it is provided that the sheet body, between the tensioning elements, extends at least partially conical and, in particular, extends in the shape of a double cone.

Further advantages, details, and features of the present invention are set forth in the hereinafter following description of several embodiments of the invention having reference to the figures of the schematic drawings.

BRIEF DESCRIPTION OF THE DRAWINGS

FIG. 4 is a schematic view of a finished assembled cover and holdback element, shown partially in section, for forming a rubber dam;

FIG. 5 is a perspective view of the rubber dam shown in FIG. 4 under an asymmetric loading;

FIG. 6 is a perspective view of one embodiment of an inventive rubber dam during its deployment in the mouth of a patient;

FIG. 7 is a side view of the rubber dam shown in FIG. 6;

FIG. 9 is a perspective elevational view, in partial section thereof, of an inventive rubber dam in another embodiment;

FIG. 10 is an enlarged perspective view of a feature of an embodiment of an inventive tensioning element;

FIG. 11 is a schematic perspective view of one step in the production of an inventive rubber dam;

FIG. 12 is a schematic perspective view of one step in the production of an inventive rubber dam;

FIG. 17 is a side view, in partial section, of the lip and cheek expander of one of the embodiments shown in FIGS. 15 and 16;

FIG. 18 is a perspective view, in partial section, of the lip and cheek expander shown in FIG. 17 in a different position thereof;

FIG. 19 is a perspective view of one step of the production of an inventive lip and cheek expander;

FIG. 20 is a perspective view of one step in the production of the inventive lip and cheek expander;

FIG. 21 is a perspective view, in partial section, of a modified sheet for an inventive rubber dam before the deployment of tensioning elements;

FIG. 22 is a perspective view of a further embodiment of a inventive rubber dam; and FIG. 23 is an enlarged sectional view of a feature of the rubber dam shown in FIG. 22.

DETAILED DESCRIPTION OF THE PREFERRED EMBODIMENTS

Figure 1:
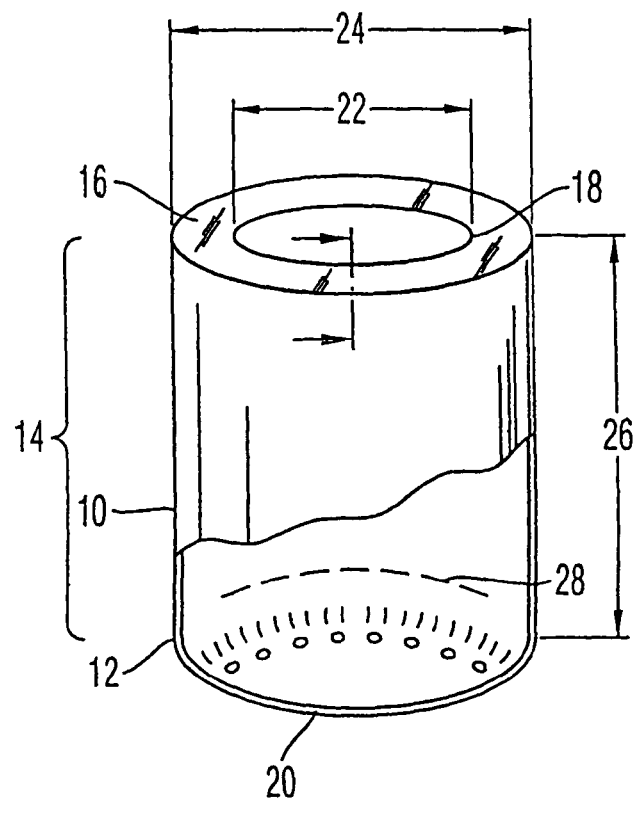
FIG. 1 is a partial view of one embodiment of the sheet body to form a rubber dam as an inventive cover and holdback element.

FIG. 1 shows a prepared sheet forming a sheet body 10 for the inventive cover and holdback element 12. The sheet is comprised, in the illustrated embodiment, of a talcum powder-free latex and has, in the illustrated embodiment, a tube-shaped portion 14. A forward end face 16 is provided with an opening 18 and a rearward end face 20 is provided with markings that can be produced either through the application of color or through pre-stamping.

The opening 18, in the illustrated example, and, as well, the cross section of the tube-shaped portion 14, are annularly-shaped. The diameter 22 of the opening is 3 cm, while the diameter 24 of the tube-shaped portion is 8 cm. The length 26 of the tube-shaped portion 14 is, in the illustrated embodiment, 6 cm and it is to be understood that the collective dimensions can, over a wide range, be accommodated to the requirements.

As is schematically shown in FIG. 1, perforations 28 can be provided, as needed, in the backside region of the tube-shaped portion 14 in order to facilitate the cutting off of the sheet body 10 at the pertaining positions or locations. Even if the sheet body 10 shown in FIG. 1 is, for all practical purposes, illustrated as a type of cylinder, it is to be understood that the sheet body is, in the practice, limp and is held in a pre-stressed form solely by the tensioning elements illustrated in FIGS. 2 and 3.

Figure 2:
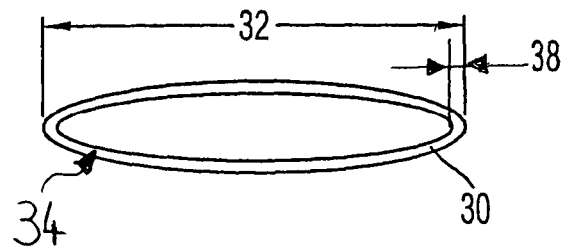
FIG. 2 is a schematic perspective view of an intra-oral spanner.
Figure 3:
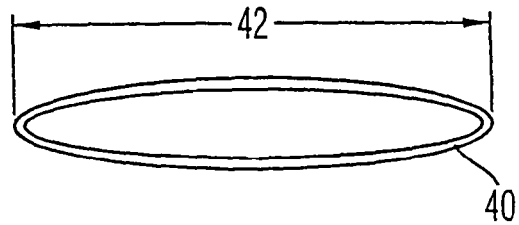
FIG. 3 is a schematic perspective view of an extra-oral spanner.

An intra-oral spanner 30 or tensioning element is shown in FIG. 2. It has a diameter 32 of 9 cm. Its cross section can deviate from an annular shape, as is illustrated in the right-hand area of FIG. 2. The intra-oral spanner 30 chas a friction area 34 that, at the least, also extends radially outwardly and serves to increase the friction relative to the tube-shaped portion 14. The retention of the desired portion of the sheet body 10 in the mouth volume of the patient is reinforced by this configuration. It is to be understood that, in lieu of this, a fully coarse tensioning element can be deployed as well; preferably, the cross sectional thickness 38 of the intra-oral spanner 30 is somewhat smaller than that of the extra-oral spanner or tensioning element 40, which is shown in FIG. 3, and has a dimension of approximately 3 mm.

In contrast, the extra-oral spanner 40 can however be configured with a thinner configuration. The extra-oral spanner 40 has a diameter 42 of approximately 10 cm and its cross sectional thickness is approximately 2 mm. It is to be understood that, as well, the dimensions can be accommodated to the requirements across a wide range.

FIG. 4 shows how an inventive rubber dam 46 can be configured. The sheet 10 extends over the intra-oral spanner 30 in such a manner that the intra-oral spanner 30 limits the closed backside or end face 20. As the diameter of the intra-oral spanner 30 is larger than the unstressed diameter of the tube-shaped portion 14, the sheet 10 is held in a tensioned condition at the location of the intra-oral spanner 30. From the intra-oral spanner 30, the sheet 10 extends radially inwardly. Thereat, a cinched-in region 50 is formed.

Continuing from the cinched-in region 50, the sheet 10 extends in an annular ring shape further to the extra-oral spanner 40. This sheet passes through the extra-oral spanner 40 from the inside and is turned there around toward the outside. The extra-oral spanner 40 places the sheet 10 in tension such that the sheet 10 is under tension thereat. The sheet 10 comprises a turnaround region 52 that extends into the cinched-in region 50. In that the sheet 10 is double-sided in the turnaround region 52, the sheet pulls itself radially inwardly even stronger thereat. The sheet terminates in the turnaround region 52 in an edge 56 that corresponds to the opening 18 shown in FIG. 1. The edge 56 can be configured in any desirable suitable manner as can be seen in FIGS. 8A-8E.

In the event of a material reinforcement of the edge 56, the radial pull force is even greater thereat. In this connection, the turnaround region 52 has a tendency to pull itself automatically into a symmetric disposition as is shown in FIG. 4. Due to the one-sided loading shown in FIG. 5 in the direction, for example, of the arrow 60, however, a portion of the sheet 10 is displaced in a self-actuated manner over the extra-oral spanner 40 such that the turnaround region 52 is smaller at that location. The turnaround region 52 thus forms, to this extent, a material reserve and, in fact, this material reserve is formed even if—as seen in FIG. 5—an axial pull force is exerted on one side on the sheet as well as even if a corresponding radial pull force is exerted on the sheet, as can happen, for example, via the lips of a patient.

The sheet automatically pulls itself back into the position shown in FIG. 4, if the pull force is no longer present, due to the reduced friction between the extra-oral spanner 40 and the side of the sheet 10 located in engagement with the extra-oral spanner 40.

It is to be understood that desirable suitable measures can be undertaken in order to reduce the friction between the extra-oral spanner and the respective side of the sheet 10 in engagement therewith—namely, the outer side of the sheet. For example, a sliding coating can be applied on the outside of the sheet 10 or talcum can be used.

FIG. 6 illustrates how a rubber dam 46 is disposed in the mouth of a patient. The extra-oral spanner 40 is bent to correspondingly follow the bent shape of the mouth. The intra-oral spanner 30 is bent even more substantially in conformity with the configuration of the mouth volume of the patient and also the cinched-in region 50 follows this shape. The backside 20 is, via the bending that occurs, no longer planar, but, instead, is tensioned over the teeth of the patient. The strongest tension in the sheet occurs along this tensioned location on the teeth of the patient so that the formation of bubbles thereat to a only very small extent need be reckoned with.

As shown in FIG. 7, the location of the rubber dam in the mouth of the patient can be seen in a side view. The intra-oral spanner 30 is, in contrast to the perspective illustration thereof shown in FIG. 6, bent in the opposite direction.

Figure 8A:
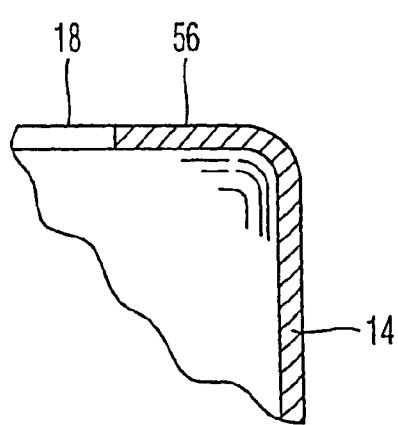
FIG. 8A is an enlarged sectional view of the edge of the sheet for an inventive cover and holdback element.
Figure 8B:
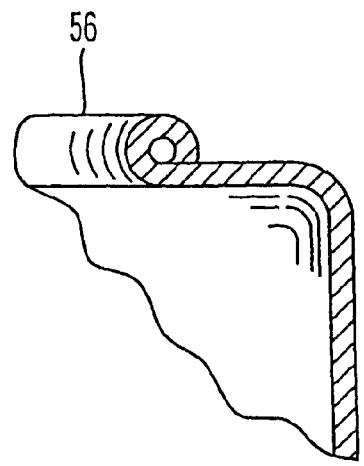
FIG. 8B is an enlarged sectional view of the edge of the sheet for an inventive cover and holdback element.
Figure 8C:
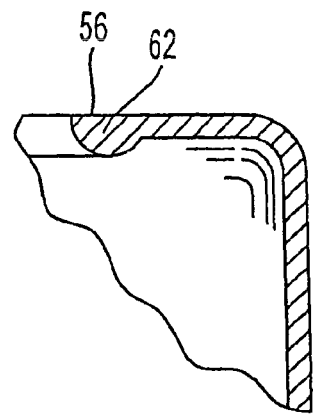
FIG. 8C is an enlarged sectional view of the edge of the sheet for an inventive cover and holdback element.
Figure 8D:
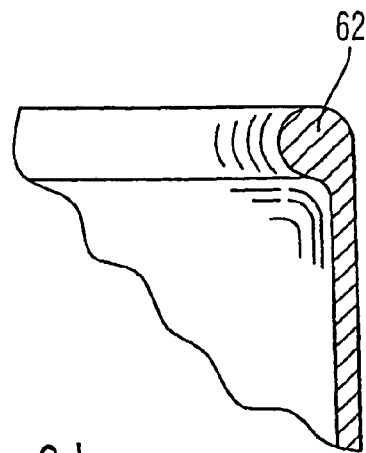
FIG. 8D is an enlarged sectional view of the edge of the sheet for an inventive cover and holdback element.
Figure 8E:
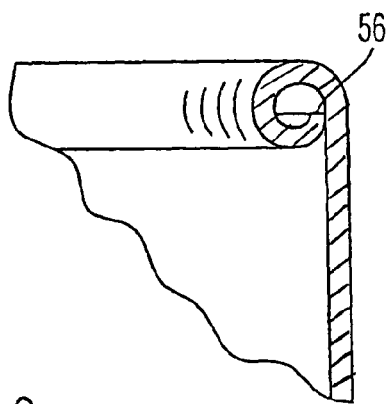
FIG. 8E is an enlarged sectional view of the edge of the sheet for an inventive cover and holdback element.

FIGS. 8a-8e show various configuration possibilities of the edge 56. FIG. 8a shows a smooth edge which the opening 18 adjoins. In contrast, FIG. 8b shows a rolled edge 56 and FIG. 8c shows a thickening 62 that forms the edge 56. In both cases, a material thickness increase is present that promotes pulling over of the edge 56 into the cinched-in region 50. FIG. 8d shows a thickening 62 in a modified form and FIG. 8e shows a rolling edge 56—an edge that is in a pre-tensioned tensioned condition when rolled up, that, upon the application of a pull force thereto, unrolls, and that, upon the release of the pull force, rolls up again.

FIG. 9 illustrates a modified configuration of an inventive rubber dam 46. In this configuration, solely an extra-oral spanner 40 is provided over which the sheet 10 is turned around and forms thereat the turnaround region 52. The sheet 10 is inserted in a bag shape through the opening 18. This configuration also makes possible the inventive displaceable disposition between sheet body and tensioning element.

FIG. 10 illustrates the manner in which the intra-oral spanner can be configured. The intra-oral spanner 30 is shown in section, whereby the surrounding material is partially removed. The intra-oral spanner 30 comprises, in this embodiment, a metallic core 66 and the surrounding material 68 is comprised of an elastic material that, at the same time, can be comparatively coarse.

FIGS. 11-14 respectively show one possible production method for an inventive rubber dam 46. In accordance with the process shown in FIG. 11, the extra-oral spanner 40 is initially inserted through the elastically configured opening 18 into the bag-shaped sheet 10. As seen in FIG. 12, the backside 20 of the bag-shaped sheet body 10 is then inserted through the opening 18, along the direction of the arrows 70 and 72, so that, at the same time, a passing of the sheet 10 through the extra-oral spanner 40 also occurs.

Figure 13:
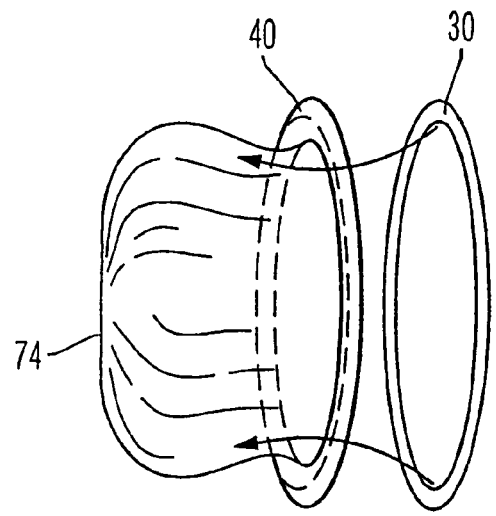
FIG. 13 is a schematic perspective view of one step in the production of an inventive rubber dam.
Figure 14:
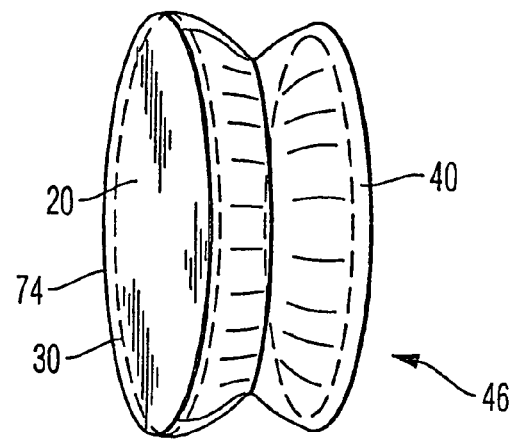
FIG. 14 is a schematic perspective view of one step in the production of an inventive rubber dam.

As shown in FIG. 13, the intra-oral spanner 30 is then inserted through the extra-oral spanner 40 and the opening 18 into the now oppositely oriented bag 74, so that there is produced the configuration of the intra-oral spanner 30 shown in FIG. 14. As can be seen, the intra-oral spanner now places the backside 20 of the bag 74 in tension.

Figure 15:
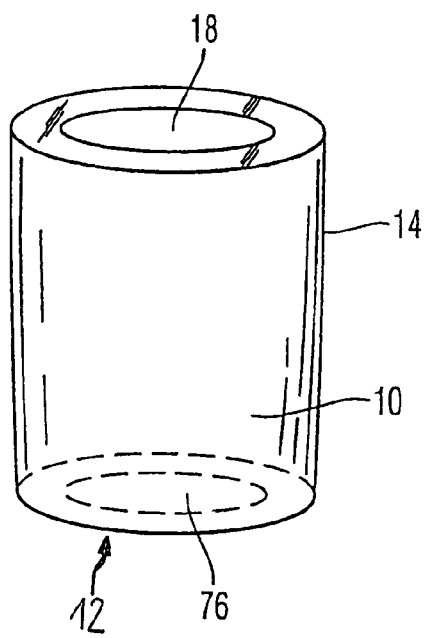
FIG. 15 is a front perspective view of a substantially annular sheet for the production of an inventive lip and cheek expander.
Figure 16:
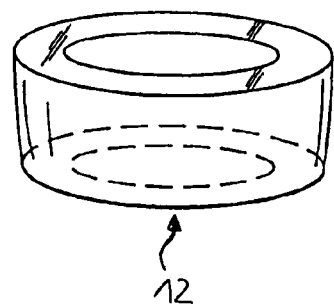
FIG. 16 is a front perspective view of a substantially annular sheet for the production of an inventive lip and cheek expander; 16

Another embodiment of the inventive cover and holdback element 10 is shown in FIGS. 15 and 16. The sheet 10 has, in addition to the opening 18, an opening 76 located in opposition to the opening 18. Here also, a tube-shaped portion 14 is formed and the sheet 10 is in a substantially cylindrical form, whereby, as shown in FIG. 15, a greater length and, as shown in FIG. 16, a reduced length, are possible.

The operation of a lip and cheek expander 80 is respectively shown in FIGS. 17 and 18. As is shown in FIG. 17, the sheet 10 extends respectively from the interior to the exterior in a turned around fashion over each of the intra-oral spanner 30 and the extra-oral spanner 40. To this extent, two turn-around regions 52 and 82 are formed.

As is shown in FIG. 18, it can be seen how the lip and cheek expander 80 deforms if an axial pull force is exerted thereon on one side as is representatively shown by the arrows 84. The sheet 10 flows from the turnaround regions 52 and 82 via playing out of the thereat provided material reserve toward the interior so that an accommodation of the sheet to the shape of the mouth of the patient occurs without additional measures. A second opening 88 in opposition to the first opening 18 can be seen in FIG. 18.

FIGS. 19 and 20 schematically illustrate the production of the lip and cheek expander 80. The sheet 10 is turned around the intra-oral spanner 30 from the interior toward the exterior. The extra-oral spanner 40 is then pushed into the tube-shaped portion 14 and, as shown in FIG. 20, the sheet is then turned around from the interior toward the exterior as representatively shown by the arrows 86.

FIG. 21 illustrates a modified embodiment of a sheet 10 for the configuration of a rubber dam 46. In the limp condition of the sheet 10 illustrated in FIG. 21, the sheet is substantially ball-shaped, whereby the opening 18 is configured in a known manner with a reinforced edge 56, and is shown by the broken lines 57. This configuration permits, as well, the inventive displaceable disposition of the extra-oral spanner 14 relative to the sheet.

A further modified embodiment of the inventive cover and holdback element is shown in FIG. 22. In this embodiment, wherein the cover and holdback element is here configured as a rubber dam but which can also be configured as a lip and cheek expander, the sheet 10 extends in the usual manner from the interior to the exterior over the extra-oral spanner 40 and extends outwardly over the intra-oral spanner 30. A roll edge 56 is provided in the cinched-in region 50 that closes off the turnaround region 52 of the sheet.

The special feature of the embodiment shown in FIG. 22 lies in the provision of additional clamping and cushioning structures 90 and 92 on the intra-oral spanner 30. The clamp 90, as is shown in an enlarged sectional view in FIG. 23, has essentially three functions:

Firstly, the provision of the additional structures on the tensioning element 30 facilitates the passing of the intra-oral spanner 30 through the opening 18 during the set up of the rubber dam. The clamp 90 or, respectively, the clamp 92, grips over the sheet as soon as the sheet is disposed on the intra-oral spanner 30.

Moreover, at this location, the pressure applied by the intra-oral spanner 30 on the mouth volume of the patient is diminished and compensated. In this connection, the clamp 90 and 92 can each be configured, at the least, from a decidedly soft synthetic material. The pressure that is exerted is, in this manner, reduced.

Additionally, the clamp 90 and 92 serves to maintain the clamping of the sheet on the intra-oral spanner 30 so that the position of the intra-oral spanner 30 relative to the sheet is fixed.

FIG. 23 illustrates the manner in which a clamp 90 can be configured. The clamp 90 comprises a clamp body 94 that extends over somewhat more than a half circle over the intra-oral spanner 30 and which firmly clamps the sheet 10 thereat. The clamp body 94 is enclosed from its exterior by a cushioning body 96. The cushioning body can be comprised, for example, of foam and, preferably, of a closed pore foam, or can be comprised of another very soft elastic and mouth tolerable plastic.

The specification incorporates by reference the disclosure of German priority document DE 10 2005 015 406.9.

The present invention is, of course, in no way restricted to the specific disclosure of the specification and drawings, but also encompasses any modifications within the scope of the appended claims.

What is claimed is:

1. A cover and holdback element for permitting disturbance-free dental operations to be performed in a patient's mouth, in particular, on a patient's teeth, comprising:
    an expandable elastic sheet (10) operable to cover at least a portion of the mouth volume of a patient;
    resilient tensioning elements (30, 40) in the form of a resilient intra-oral spanner (30) and a resilient extra-oral spanner (40), the sheet (10) having at least one opening (18), an end portion of the sheet adjacent the opening being turned around and folded about the extra-oral spanner (40) and thereby forming an adjustable sheet reserve which is unattached to and may freely slide back and forth in a longitudinal direction against and with respect to the portion of said elastic sheet extending between said intra-oral expander (30) and said extra-oral expander (40), said sheet reserve automatically lengthening or shortening in response to the amount of tension applied to said elastic sheet as said cover and holdback element is manipulated in the patient's mouth.

2. A cover and holdback element according to claim 1, wherein the largest clear space of the opening (18) is larger than the smallest clear space of the expandable sheet (10).

3. A cover and holdback element according to claim 1, wherein the expandable sheet (10) has an edge that encircles the opening (18), the edge having the same thickness as the expandable sheet (10) and the edge being a selected one of a thickened edge and an edge in the form of a collar.

4. A cover and holdback element according to claim 1, wherein the expandable sheet (10) is configured as a rubber dam (46) that is closed off at the end thereof opposite said opening, and wherein the expandable sheet (10) extends outwardly radially around the intra-oral spanner 30.

5. A cover and holdback element according to claim 1, wherein said sheet reserve assists in radially cinching the expandable sheet (10) between the tensioning elements (30, 40) and thereby forming a cinched-in region (50).

6. A cover and holdback element according to claim 5, wherein the position of a longitudinal extent of the cinched-in region (50) that extends, parallel to a middle longitudinal axis of the resilient tensioning elements (30, 40) can be varied relative to one of the tensioning elements (30, 40) via displacement of said sheet reserve.

7. A cover and holdback element according to claim 1, wherein the intra-oral spanner (30) is annularly shaped and, in particular, the intra-oral spanner (30) has a diameter that is around 2 to 20% and, especially, approximately 5 to 10%, smaller than that of the extra-oral spanner (40).

8. A cover and holdback element according to claim 1, wherein the expandable sheet (10) has at least one of a wall thickness of 10 mm to 2 mm and an expansion capability to expand to 1.5 to 7 times its original size.

9. A cover and holdback element according to claim 1, wherein the at least one tensioning element (30, 40) is comprised of at least one of spring steel, plastic, and glass fibers, and, especially, has a cross sectional thickness of 0.5 to 5 mm.

10. A cover and holdback element according to claim 1, wherein the resilient tensioning element (30, 40) is at least partially encased with an elastic material.

11. A cover and holdback element according to claim 1, wherein the expandable sheet (10) is formed of a selected one of latex and polyurethane.

12. A cover and holdback element according to claim 1, wherein the expandable sheet (10) comprises at least one of pre-stamped, pre-marked and perforated regions to facilitate tearing of said sheet at a perforated region to allow the patient's teeth to be worked upon to pass through said elastic material at said torn perforated region.

* * * * *